US00PP22001P2

(12) United States Plant Patent
Koeneman et al.

(10) Patent No.: US PP22,001 P2
(45) Date of Patent: Jul. 5, 2011

(54) ***MALUS* TREE NAMED 'BAILEARS'**

(50) Latin Name: ***Malus* hybrid**
Varietal Denomination: Bailears

(75) Inventors: Jon W. Koeneman, New Haven, IN (US); Michael K. Koeneman, New Haven, IN (US)

(73) Assignee: Bailey Nurseries, Inc., Newport, MN (US)

( * ) Notice: Subject to any disclaimer, the term of this patent is extended or adjusted under 35 U.S.C. 154(b) by 0 days.

(21) Appl. No.: 12/800,274

(22) Filed: May 12, 2010

(51) Int. Cl.
*A01H 5/00* (2006.01)

(52) U.S. Cl. ..... Plt./161

(58) Field of Classification Search ..... Plt./161
See application file for complete search history.

*Primary Examiner* — Annette Para
(74) *Attorney, Agent, or Firm* — Penny J. Aguirre

(57) ABSTRACT

A new and distinctive cultivar of flowering crabapple, *Malus* 'Bailears', that is characterized by its small stature, its weeping habit, its foliage that is burgundy in color when emerging and changes to burgundy green in color as the leaves mature, its abundance of purple-pink flowers opening from deep pink buds, and its dark red fruit that is persistent into winter, and its hardiness in U.S.D.A. Zones 4 to 7.

2 Drawing Sheets

Botanical classification: *Malus* hybrid.
Variety denomination: 'Bailears'.

BACKGROUND OF THE INVENTION

The present invention relates to a new and distinct cultivar of *Malus* of hybrid origin and will be referred to hereafter by its cultivar name, 'Bailears'. 'Bailears' is a deciduous tree grown for use as an ornamental landscape plant.

The new cultivar, 'Bailears', was discovered as a whole plant mutation in 2004 by the Inventors in a trial garden at a nursery in New Haven, Ind. The parentage is unknown. The cultivars 'Louisa' (not patented) and 'Prairiefire' (not patented) are probable parents based on their characteristics and their proximity to the new cultivar in the trial garden.

Asexual reproduction of the new cultivar was first accomplished by budding onto *Malus columbia* rootstock under the direction of the Inventors in 2007 in St. Paul, Minn. The characteristics of this cultivar have been determined to be stable and are reproduced true to type in successive generations.

SUMMARY OF THE INVENTION

The following traits have been repeatedly observed and represent the characteristics of the new cultivar as observed for the original tree as grown in New Haven, Ind., as well as upon the asexually budded progeny in Minnesota. These attributes in combination distinguish 'Bailears' as a unique cultivar of *Malus*.

1. 'Bailears' exhibits a small stature and weeping habit.
2. 'Bailears' exhibits foliage that is burgundy in color when emerging and changes to burgundy green in color as the leaves mature.
3. 'Bailears' exhibits profuse flowering with deep pink buds opening to purple-pink blossoms in spring.
4. 'Bailears' exhibits dark red fruit that is persistent into winter.
5. 'Bailears' exhibits hardiness in U.S.D.A. Zones 4 to 7.

The new cultivar can be compared to cultivars 'Louisa', 'Prairiefire', and 'Coral Cascade' (U.S. Plant Pat. No. 7,7142). 'Louisa' is similar to 'Bailears' in having a weeping habit but differs from 'Bailears' in having green colored foliage, flowers that are lighter pink in color and fruit that is yellow in color. 'Prairiefire' is similar in foliage color to 'Bailears' but differs from 'Bailears' in being taller and wider in plant size, in having an upright habit (non weeping), and in having maroon colored fruit. 'Coral Cascade' is similar to 'Bailears' in having a weeping habit but differs from 'Bailears' in having green colored foliage and reddish orange colored fruit.

BRIEF DESCRIPTION OF THE DRAWING

The accompanying colored photographs illustrate the overall appearance and distinct characteristics of the new *Malus* as grown in Oregon, Indiana and Minnesota. The plants in the photograph are about 5 years in age with 'Bailears' budded onto *Malus columbia* rootstock.

Figure 1:
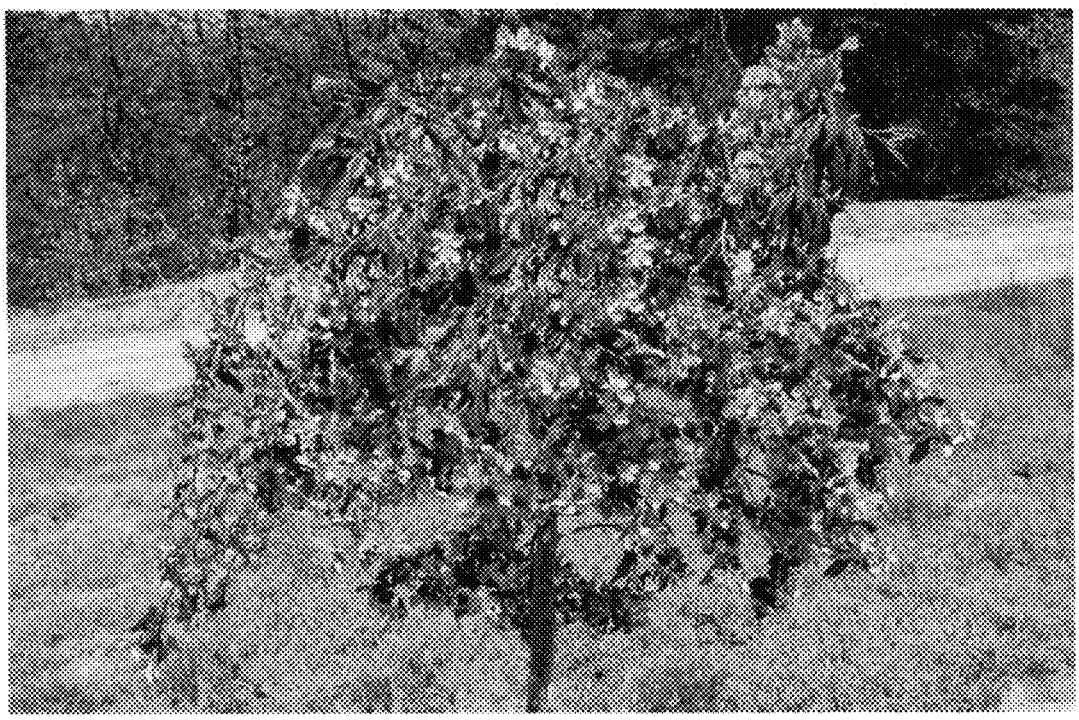
FIG. 1 is a side view of a plant of 'Bailears' and illustrates its profuse flowering and weeping habit.
Figure 2:
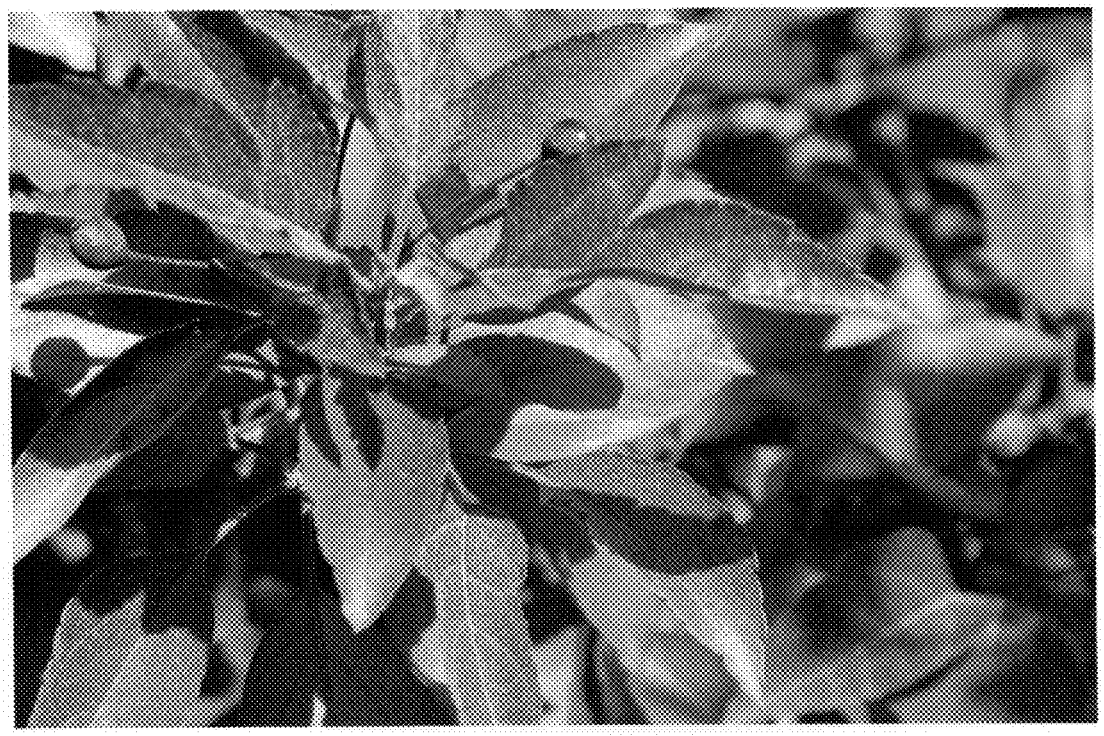
FIG. 2 provides a close-up view of the newly emerged foliage of 'Bailears'.
Figure 3:
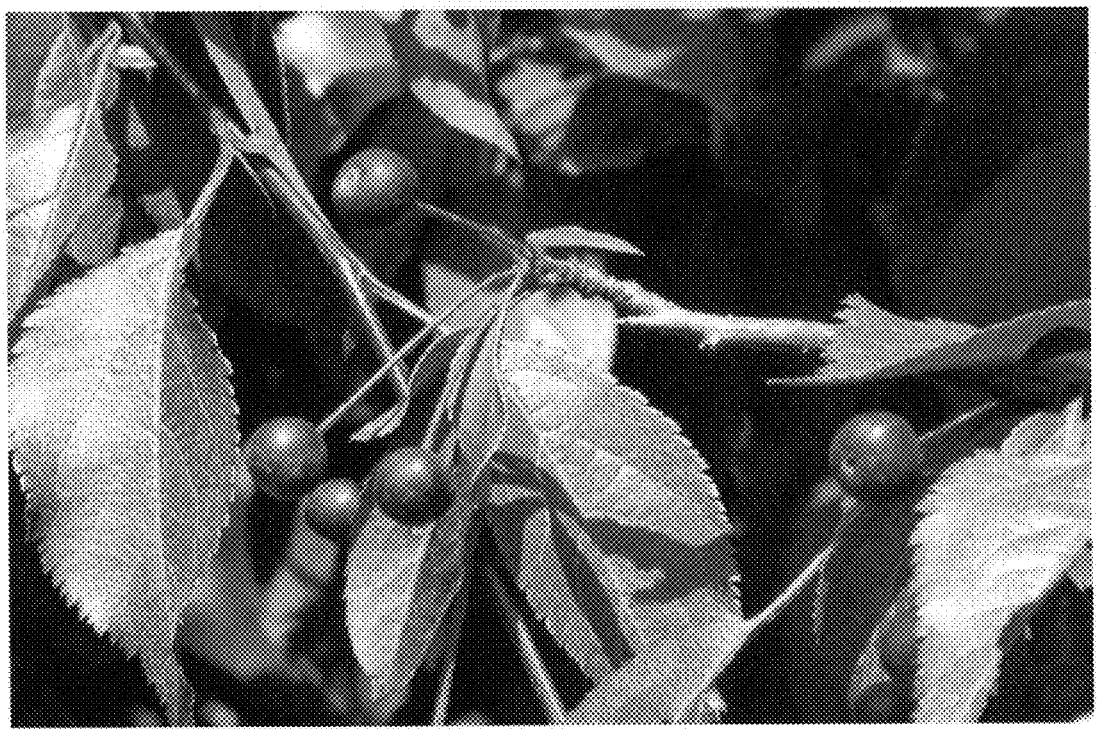
FIG. 3 provides a close-up view of the fruit and mature leaves of 'Bailears'.

The colors in the photographs are as close as possible with the digital photography techniques available, the color values cited in the detailed botanical description accurately describe the colors of the new *Malus*.

DETAILED BOTANICAL DESCRIPTION

The following is a detailed description of the new cultivar as observed for a four year-old tree (with rootstock) of 'Bailears' as grown on *Malus columbia* rootstock outdoors in St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Tree description:

*Tree habit.*—Main stem upright with cascading lateral branches.

*Height and spread.*—A mature plant reaches about 2.4 m to 2.5 m (8 to 10 ft) in height and 3.6 to 4.6 m (12 to 15 ft) in width.

*Diseases and pests.*—No particular resistance or susceptibility has been observed to date.

*Hardiness.*—U.S.D.A. Zones 4 to 7.

*Branching habit.*—Numerous lateral and 3 to 4 secondary lateral branches per lateral branch, primarily alternate, emerge nearly horizontal and cascade downward at an average angle of 45°, lateral branches are an average of 1 m in length and 3 mm in width, secondary lateral branches are an average of 48 cm in length and 2.5 mm in width.

*Propagation.*—Budding onto *Malus columbia* rootstock.

*Time required for graft development.*—About 4 weeks to develop in a 36-cell tree pot.

*Growth rate.*—Moderate, grows about 40.4 cm (15.9 inches) per year.

*Trunk.*—About 3 cm in width on four year-old plant (measured at 20 cm from base of tree), bark is 200D in color overlaid with 198C with horizontal lenticels (about 3 per sq. cm, about 3 mm in length and 1.5 mm in width) 165D in color.

Description of dormant shoots (one year old):

*Pubescence on upper side.*—Medium.

*Shine of bark.*—Weak.

*Thickness of shoot at center of middle internode.*—Average of 4 mm.

*Bark color.*—A color between 200B and N186C.

*Shoot angle.*—Horizontal and then cascading to approximately 45°.

*Lenticels.*—About 3 per square cm of trunk, an average of 3 mm in length and 1.5 mm in width, 165D in color.

Description of new growth:

*Color.*—N186C.

*Pubescence.*—Heavy on growth tips and moderate on lower portion of branch, 189D in color.

*Lenticels.*—About 5 per 4 sq. mm of new branch growth, 161A in color and an average of 0.7 mm in length and 0.4 mm in width.

Leaf description:

*Leaf orientation.*—Outward to slightly pendent.

*Leaf division.*—Simple.

*Leaf shape.*—Elliptic to lanceolate.

*Leaf size.*—Average of 7.6 cm in length and 3.2 cm in width ($4^{th}$ to $6^{th}$ leaf).

*Leaf apex.*—Acuminate.

*Leaf base.*—Cuneate.

*Leaf surface.*—Glabrous and semi-glossy on upper surface and glabrous and dull on lower surface.

*Leaf margin.*—Finely serrated.

*Leaf color.*—New growth upper surface; 146A and heavily suffused with 166A, new growth lower surface; 146A and suffused with 166A, mature growth upper surface; 147A, mature growth lower surface; 147B and slightly suffused with 166A, fall color upper surface; blend of 79A and 187A.

*Leaf venation.*—Pinnate main veins with netted minor veins, only midrib on lower surface is prominent, upper and lower surface 165D in color, surface of mid rib on upper surface and pinnate veins on lower surface tomentose.

*Petioles.*—Average of 2 cm in length and 1.5 mm in diameter, tomentose surface, upper surface is 187A in color and heavily covered with pubescence 189D in color, lower surface is 165D in color.

*Stipules.*—2 per petiole, 79A in color, an average of 1.3 cm in length and 4 mm in width, glabrous on upper and lower surface, color is 147A on upper surface and 147B on lower surface.

Flower description:

*Flowering period.*—Early to mid season.

*Beginning flowering date.*—Typically about May $10^{th}$ in Manitoba.

*Number of flowers.*—Average of 5 per cluster and 80 per branch that is 100 cm in length.

*Inflorescence type.*—Corymb of rotate flowers.

*Flower buds.*—59B to 59D in color prior to opening, round in shape, average of 1 cm in length and 1 cm in diameter.

*Flower size.*—Average of 3.5 cm in diameter and 1.5 cm in depth.

*Flower fragrance.*—Mild.

*Flower aspect.*—Outward.

*Petals.*—5 per flower, un-fused, partially overlapping, ovate to obovate in shape, rounded to truncate apex, attenuate base, entire margin, about 1.7 cm in length and 1.2 cm in width, upper and lower surface 64A to 64D turning 65C in color with veins and margins 64C as petals age, lower surface semi-glossy.

*Sepals.*—5 per flower, alternate with petals, lanceolate in shape, fused at base, apex acute, reflexed, margins entire, pubescent, lower surface glabrous, 64B in color 191C toward margin, upper surface pubescent, 189B in color.

*Pedicel.*—184A in color, average of 4 cm in length and 1 mm in width, surface is strongly pubescent.

*Pistil.*—Compound carpel, 1.2 cm in length, 3 mm in width, style is 60A in color and 7 mm in length, 0.5 mm in width, 5 stigmas fused at base, 160A to 145B in color, ovary pubescent 160A in color.

*Stamens.*—About 20 per flower, anther oblong in shape, 18A in color and 1.5 mm in length, 1 mm in width, filaments 1 to 6 mm in length, 1 mm in width, 59C to 73D in color, pollen is 4A in color and moderate in quantity.

Fruit description:

*Shape.*—Round.

*Size.*—Average of 9 mm in diameter.

*Quantity.*—1 to 2 per node on terminal 4 nodes of branches.

*Skin.*—Smooth and glossy surface and color is 178A when mature and dries to 177A.

*Flesh.*—Texture dense and dry, color is a blend of 59C and 144D.

*Fruit presence and longevity.*—Late summer and persistent into winter.

*Stalk.*—An average of 2 cm in length and 1 mm in diameter, surface is glabrous.

*Seed.*—Kidney-shaped, glossy in appearance, 2 per fruit, about 4 mm in length and 2 mm in width, 60C in color.

It is claimed:

1. A new and distinct cultivar of *Malus* tree named 'Bailears' as herein illustrated and described.

* * * * *